United States Patent [19]

Treiber et al.

[11] Patent Number: 5,342,839
[45] Date of Patent: Aug. 30, 1994

[54] 2-HYDROXY-3-PHENOXY-PROPYL-SUBSTITUTED PIPERAZINES, THEIR PREPARATION AND USE

[75] Inventors: Hans-Joerg Treiber, Bruehl; Hans P. Hofmann, Limburgerhof; Laszlo Szabo, Heidelberg; Liliane Unger, Ludwigshafen; Manfred Raschack, Weisenheim am Sand, all of Fed. Rep. of Germany

[73] Assignee: BASF Aktiengesellschaft, Ludwigshafen, Fed. Rep. of Germany

[21] Appl. No.: 659,365

[22] PCT Filed: Sep. 12, 1989

[86] PCT No.: PCT/EP89/01058
§ 371 Date: Mar. 18, 1991
§ 102(e) Date: Mar. 18, 1991

[87] PCT Pub. No.: WO90/03371
PCT Pub. Date: Apr. 5, 1990

[30] Foreign Application Priority Data

Sep. 21, 1988 [DE] Fed. Rep. of Germany ....... 3831993

[51] Int. Cl.$^5$ ................ A61K 31/495; A61K 31/55; C07D 295/088; C07D 243/08
[52] U.S. Cl. .................... 514/255; 514/218; 540/575; 544/396
[58] Field of Search ............. 544/396; 514/255, 218; 540/575

[56] References Cited

U.S. PATENT DOCUMENTS

| 3,133,925 | 5/1964 | Cusic | 544/396 |
| 4,361,562 | 11/1982 | Berthold | 514/253 |
| 4,831,028 | 5/1989 | Lerch et al. | 514/224.2 |
| 5,087,627 | 2/1992 | Morita et al. | 544/396 |

FOREIGN PATENT DOCUMENTS

| 0068324 | 1/1983 | European Pat. Off. |  |
| 1317034 | 5/1973 | United Kingdom . |  |
| 05165 | 4/1992 | World Int. Prop. O. | 544/396 |

Primary Examiner—Emily Bernhardt

[57] ABSTRACT

2-Hydroxy-3-phenoxy-propyl-substituted piperazines of the formula I

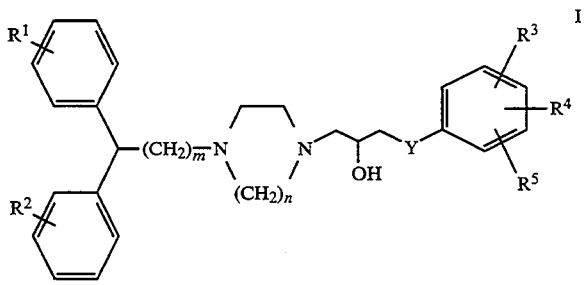

in which $R^1$–$R^5$, Y, m and n have the meaning indicated in the description, and the preparation thereof are described. The novel compounds are suitable for the therapy of oxygen deficiency diseases of the brain.

6 Claims, No Drawings

2-HYDROXY-3-PHENOXY-PROPYL-SUBSTITUTED PIPERAZINES, THEIR PREPARATION AND USE

DESCRIPTION

The invention relates to 2-hydroxy-3-phenoxypropyl-substituted piperazines and homopiperazines, processes for the preparation thereof and the use thereof as drugs.

Numerous piperazines of various types have already been disclosed. Thus, for example, flunarizine and lidoflazine from the benzhydryl- and diarylbutylpiperazine series have been disclosed as therapeutics for cardiovascular and cerebrovascular disorders. Their mode of action is based on inhibition of the influx of calcium into the cell.

This mechanism of action also applies to the ω-phenoxy-alkyl-piperazines described in DE-A 3.600.390. The therapeutic aim of these compounds is, just like that of the benzhydryl-phenylalkanol-substituted piperazines described in DE-A 3.326.148, to treat disorders of the cerebral circulation.

N-Arylpiperazinealkanamides with diarylbutyl substituents on the piperazine ring (cf. EP-A 68544) improve the blood supply to the heart and protect it from the consequences of an ischemia, anoxia or hypoxia.

3-Aryloxy-2-propanol derivatives of phenylpiperazine have also been disclosed, but they display no calcium-antagonistic or antihypoxic effects (Arzneim. Forsch. (1978) 28 241–246).

It has now been found that 2-hydroxy-3-phenoxypropyl-substituted piperazines or homopiperazines of the formula I

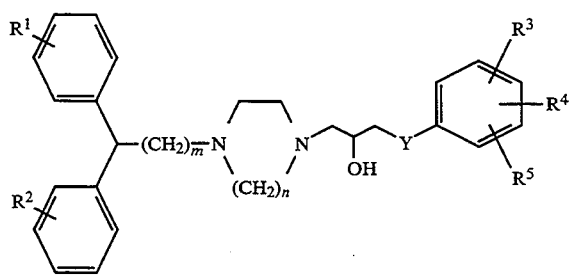

in which
R$^1$ and R$^2$ denote hydrogen, fluorine or chlorine atoms, methoxy, methyl or trifluoromethyl groups,
R$^3$, R$^4$ and R$^5$ denote hydrogen, fluorine or chlorine atoms, methyl, trifluoromethyl, cyano or nitro groups or a saturated or unsaturated alkoxy group with up to 3 C atoms,
Y denotes an oxygen or sulfur atom,
m denotes 1, 2 or 3 and
n denotes 2 or 3,
are strong calcium antagonists which have a pronounced cerebral antihypoxic effect and which significantly improve the regional blood supply to the brain.

Thus the compounds according to the invention appear to be suitable for the therapy of cardiovascular disorders in general and in particular for treating acute and chronic oxygen deficiency states of the brain. By this are meant acute hypoxic or ischemic states occurring, for example, following cerebral infarct, craniocerebral trauma or vasospasms and following cardiovascular failure, e.g. associated with cardiac arrest, cardiac arrhythmias or circulatory failure. Examples of relevant syndromes with chronic oxygen deficiency states are: transient ischemic attacks (TIAs) and prolonged reversible ischemic neurological deficits (PRINDs), as well as multiinfarct dementia and atherosclerotic dementia, besides migraine and epilepsies.

Suitable physically tolerated acids are: inorganic acids such as hydrochloric acid, sulfuric acid, phosphoric acid, nitric acid or organic acids such as tartaric acid, lactic acid, malic acid, citric acid, maleic acid, fumaric acid, oxalic acid, acetic acid, gluconic acid or mucic acid.

In the formula I, R$^1$ and R$^2$ are preferably hydrogen, fluorine or chlorine atoms, R$^3$ and R$^4$ are preferably hydrogen atoms, while R$^5$ is, in particular, a fluorine or chlorine atom. n is preferably 2 and m is preferably 2 or 3. Y is, in particular, an oxygen atom. The substituents R$^1$, R$^2$ and R$^5$ are, in particular, located in the 3 or 4 position of the phenyl rings. The 4 positions are preferred.

The compounds of the formula I have a center of chirality in the structural element of the aryloxypropanol. They therefore exist in the form of optical antipodes (enantiomers). The racemates can be obtained by conventional methods by salt formation with chiral auxiliary components such as dibenzoyltartaric acid, fractional crystallization and subsequent liberation of the bases from the salts or else by synthesis from suitable chiral precursors.

The invention also relates to processes for preparing the compounds of the formula I, which comprise reacting either a) a compound of the formula II

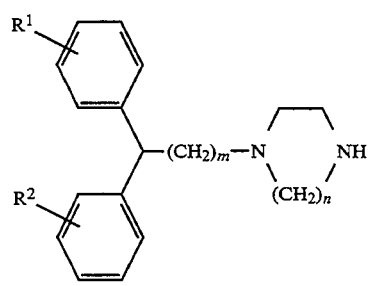

in which R$^1$, R$^2$, m and n have the stated meaning, with an epoxide of the formula III

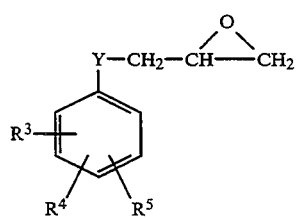

in which Y, R$^3$, R$^4$ and R$^5$ have the stated meaning,
or
b) a compound of the formula IV

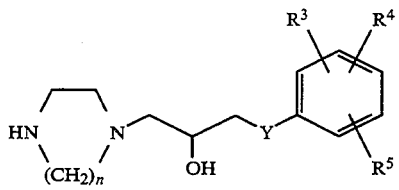

in which Y, $R^3$, $R^4$, $R^5$ and n have the stated meaning, with a compound of the formula V

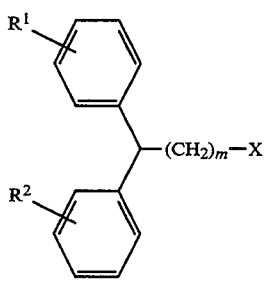

where $R^1$, $R^2$, and m have the stated meaning, and X denotes a reactive acid residue. The compounds obtained in this way can then be converted with physiologically tolerated acids into their salts.

The reaction, which is known per se, of epoxides of the formula III with secondary amines of the formula II is expediently carried out in a solvent such as acetonitrile, dimethylformamide, tetrahydrofuran or a lower alcohol, preferably methanol or ethanol, at elevated temperatures (30°–120° C.), preferably at the boiling points of the solvent.

Process b) is preferably carried out in a polar organic solvent such as alcohols, e.g. methanol, ethanol, isopropanol or a lower ketone, preferably acetone, methyl ethyl ketone or methyl isobutyl ketone or in dimethylformamide. Dimethyl sulfoxide, acetonitrile, where appropriate also in a hydrocarbon such as toluene, advantageously in the presence of an auxiliary base to trap the acid which is formed, such as, for example, sodium carbonate, potassium carbonate, calcium carbonate, triethylamine or pyridine at elevated temperature, preferably between 20° and 120° C. Suitable reactive acid residues X are chlorine, bromine or iodine atoms and sulfonic acid groups, preferably methanesulfonyl, benzenesulfonyl, p-toluenesulfonyl or trifluoromethanesulfonyl radicals.

The starting compounds of the formula II to V are known from the literature or can be prepared analogously in a manner known per se. Thus, reaction of optically active (R)- or (S)-epichlorohydrin with phenols or thiophenols of the formula VI

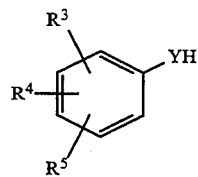

in which Y, $R^3$, $R^4$ and $R^5$ have the stated meanings, results in optically active epoxides of the formula III which can be reacted with the compounds of the formula II to give optically active compounds of the formula I.

The compounds according to the invention can be administered in a customary manner orally, rectally or parenterally (subcutaneously, intravenously, intramuscularly, transdermally). Administration can also take place through the nasopharyngeal space with vapors or sprays.

The dosage depends on the age, condition and weight of the patient and on the mode of administration. As a rule, the daily dose of active substance is between about 0.1 and 20 mg/kg of body weight on oral administration and between about 0.01 and 2 mg/kg of body weight on parenteral administration. In the normal case, satisfactory results are achieved with daily doses of 10–100 mg orally and 1–10 mg parenterally.

The novel compounds can be used solid or liquid in the conventional pharmaceutical administration forms, e.g. as tablets, film-coated tablets, capsules, powders, granules, sugar-coated tablets, suppositories, solutions, ointments, creams, sprays or transdermal therapeutic systems. These are prepared in a conventional manner. This may entail the active substances being processed with the conventional pharmaceutical auxiliaries such as tablet binders, fillers, preservatives, tablet disintegrants, flow regulators, plasticizers, wetting agents, dispersants, emulsifiers, solvents, retardants antioxidants and/or propellant gases (cf. H. Sucker et al.: Pharmazeutische Technologie, Thieme-Verlag, Stuttgart, 1978). The administration forms obtained in this way normally contain the active substance in an amount of from 1 to 75% by weight.

EXAMPLES 1.  1-[4,4-bis(4-Fluorophenyl)butyl]-4-[2-hydroxy-3(4-chlorophenoxy)propyl]piperazine 6.6 g (0.02 mol) of 1-[4,4-bis(4-fluorophenyl)]-butyl-piperazine and 3.7 g (0.02 mol) of 3-(4-chlorophenoxy)-1,2-epoxypropane in 100 ml of ethanol were heated to boiling under reflux for 2 h. After cooling, the solvent was removed by distillation under reduced pressure. Ethereal hydrochloric acid added to the oily residue, the precipitate filtered off with suction and the product recrystallized with isopropanol/water. Yield: 5.2 g di-hydrochloride $C_{29}H_{33}ClF_2N_2O_2 \cdot 2HCl$, melting point 205°–211° C.

The following were prepared analogously:

2.  1-[4,4-bis(4-fluorophenyl)butyl]-4-[2-hydroxy-3(4-fluorophenoxy)propyl]piperazine, di-hydrochloride $C_{29}H_{33}F_3N_2O_2 \cdot 2HCl$, melting point 225°–227° C., 3.  1-[4,4-bis(4-fluorophenyl)butyl]-4-[2-hydroxy-3-phenoxypropyl]piperazine, di-hydrochloride $C_{29}H_{34}F_2N_2O_2 \cdot 2HCl$, melting point 237°–240° C.

4.  1-[4,4-diphenylbutyl]-4-[2-hydroxy-3-phenoxypropyl]-piperazine, di-hydrochloride $C_{29}H_{36}N_2O_2 \cdot 2HCl$, melting point 237°–242° C.

5.  1-[4,4-bis(4-fluorophenyl)butyl]-4-[2-hydroxy-3-(2-methoxyphenoxy)propyl]piperazine, di-hydrochloride $C_{30}H_{36}F_2N_2O_2 \cdot 2HCl$, melting point 199°–201° C.

6.  1-[4,4-bis(4-fluorophenyl)butyl]-4-[2-hydroxy-3-(2-allyloxyphenoxy)propyl]piperazine, di-hydrochloride $C_{32}H_{38}F_2N_2O_3 \cdot 2HCl$, melting point 154°–156° C.

7.  1-[3,3-diphenylpropyl]-4-[2-hydroxy-3-phenoxypropyl]piperazine, di-hydrochloride $C_{28}H_{34}N_2O_2 \cdot 2HCl$, melting point 242°–250° C.

8. 1-[3,3-diphenylpropyl]-4-[2-hydroxy-3(4-chlorophenoxy)propyl]piperazine, di-hydrochloride $C_{28}H_{33}ClN_2O_2 \cdot 2HCl$, melting point 235°–240° C.

9. 1-[2,2-diphenylethyl]-4-[2-hydroxy-3-(4-chlorophenoxy)propyl]piperazine, di-hydrochloride $C_{27}H_{29}Cl_3N_2O_3 \cdot 2HCl$, melting point 240°–245° C.

10. 1-[4,4-bis(4-trifluoromethylphenyl)butyl]-4-[2-hydroxy-3-(4-fluorophenoxy)propyl]piperazine, di-hydrochloride $C_{31}H_{31}F_7N_2O_2 \cdot 2HCl$, melting point 195°–198° C.

11. 1-[4,4-bis(4-fluorophenyl)butyl]-4-[2-hydroxy-3(3-trifluoromethylphenoxy)propyl]piperazine, di-hydrochloride $C_{30}H_{33}F_5N_2O_2 \cdot 2HCl$, melting point 180°–185° C.

12. 1-[4,4-bis(4-fluorophenyl)butyl]-4-[2-hydroxy-3-(3,4-dichlorophenoxy)propyl]piperazine, di-hydrochloride $C_{29}H_{32}Cl_2F_2N_2O_2 \cdot 2HCl$, melting point 202°–209° C.

13. 1-[4,4-bis(4-fluorophenyl)butyl]-4-[2-hydroxy-3-(c-chlorophenoxy)propyl]piperazine, di-hydrochloride $C_{29}H_{33}ClF_2N_2O_2 \cdot 2HCl$, melting point 205°–211° C.

14. 1-[4,4-bis(4-fluorophenyl)butyl]-4-[2-hydroxy-3-(4-methylphenoxy)propyl]piperazine, di-hydrochloride $C_{30}H_{36}F_2N_2O_2 \cdot 2HCl$, melting point 229°–235° C. 15. 1-[4,4-bis(4-fluorophenyl)butyl]-4-[2-hydroxy-3(3,4-dimethylphenoxy)propyl]piperazine, di-hydrochloride $C_{31}H_{38}F_2N_2O_2 \cdot 2HCl$, melting point 224°–229° C.

16. 1-[4,4-bis(4-fluorophenyl)butyl]-4-[2-hydroxy-3-(4-nitrophenoxy)propyl]piperazine, di-hydrochloride $C_{29}H_{33}F_3N_3O_4 \cdot 2HCl$, melting point 217°–224° C.

17. 1-[4,4-bis(4-fluorophenyl)butyl]-4-[2-hydroxy-3-(2-cyanophenoxy)propyl]piperazine, di-hydrochloride $C_{30}H_{33}F_2N_3O_2 \cdot 2HCl$, melting point 216°–224° C.

18. 1-[4,4-bis(4-trifluoromethylphenyl)butyl]-4-[2-hydroxy-3-(3-chlorophenoxy)propyl]piperazine, dihydrochloride $C_{31}H_{31}ClF_6N_2O_2 \cdot 2HCl$, melting point 190°–195° C., 19. 1-[4,4-bis(4-trifluoromethylphenyl)butyl]-4-[2-hydroxy-3-(3,4-dichlorophenoxy)propyl]piperazine, di-hydrochloride $C_{31}H_{30}Cl_2F_6N_2O_2 \cdot 2HCl$, melting point 190°–197° C., 20. 1-[4,4-bis(4-trifluoromethylphenyl)butyl]-4-[2-hydroxy-3-(3-trifluoromethylphenoxy)propyl]piperazine, di-hydrochloride $C_{32}H_{31}F_9N_2O_2 \cdot 2HCl$, melting point 193°–200° C., 21. 1-[4,4-bis(4-trifluoromethylphenyl)butyl]-4-[2-hydroxy-3-(4-nitrophenoxy)propyl]piperazine, di-hydrochloride $C_{31}H_{31}F_6N_3O_4 \cdot 2HCl$, melting point 124°–127° C. (amorphous), 22. 1-[4,4-diphenylbutyl]-4-[2-hydroxy-3-(4-fluorophenoxy)propyl]piperazine, di-hydrochloride $C_{29}H_{35}FN_2O_2 \cdot 2HCl$, melting point 198°–201° C.

23. 1-[4,4-diphenylbutyl]-4-[2-hydroxy-3-(3,4-dichlorophenoxy)propyl]piperazine, di-hydrochloride $C_{29}H_{34}Cl_2N_2O_2 \cdot 2HCl$, melting point 200°–205° C.

24. 1-[4,4-bis(4-methylphenyl)butyl]-4-[2-hydroxy-3-(4-fluorophenoxy)propyl]piperazine, di-hydrochloride $C_{31}H_{39}FN_2O_2 \cdot 2HCl$, melting point 192°–196° C.

25. 1-[4,4-bis(4-methoxyphenyl)butyl]-4-[2-hydroxy-3-phenoxypropyl]piperazine, di-hydrochloride $C_{31}H_{40}N_2O_2 \cdot 2HCl$, melting point 214°–216° C.

26. 1-[4,4-bis(4-methoxyphenyl)butyl]-4-[2-hydroxy-3-(3.4.5-trimethoxyphenoxy)propyl]piperazine, dihydrochloride $C_{34}H_{46}N_2O_7 \cdot 2HCl$, melting point 190°–193° C.

27. 1-[4,4-bis(3-fluorophenyl)butyl]-4-[2-hydroxy-3-(4-fluorophenoxy)propyl]piperazine, di-hydrochloride $C_{24}H_{33}F_3N_2O_2 \cdot 2HCl$, melting point 222°–225° C.

28. 1-[4,4-bis(4-chlorophenyl)butyl]-4-[2-hydroxy-3-(4-chlorophenoxy)propyl]piperazine, di-hydrochloride $C_{29}H_{33}Cl_3N_2O_2 \cdot 2HCl$, melting point 190°–196° C.

The following were obtained by reacting the enantiomers 3-(4-fluorophenoxy)-1,2-epoxy-propanes (obtained by synthesis from 4-fluorophenol and (R)- or (S)-epichlorohydrin) with 1-[4,4-bis(4-fluorophenyl)-butyl]piperazine in analogy to Example 1:

29. (−)-1[4,4-bis(4-fluorophenyl)butyl]-4-[2-hydroxy-3(4-fluorophenoxy)propyl]piperazine, dihydrochloride $C_{29}H_{33}F_3N_2O_2 \cdot 2HCl$, melting point 208°–216° C., $[\alpha]_{589\ mm}^{20} = -9.4°$ (methanol, 10 mg/ml), 30. (+)-1[4,4-bis(4-fluorophenyl)butyl]-4-[2-hydroxy-3(4-fluorophenoxy)propyl]piperazine, di-hydrochloride $C_{29}H_{33}F_3N_2O_2 \cdot 2HCl$, melting point 208°–216° C., $[\alpha]_{589\ mm}^{20} = -9.4°$ (methanol, 10 mg/ml), 31. (−)-1(3,3-diphenylpropyl)-3-[2-hydroxy-3(4-fluorophenoxy)propyl]piperazine, di-hydrochloride $C_{28}H_{33}FN_2O_2 \cdot 2HCl$, melting point 230°–233° C., $[\alpha]_{589\ mm}^{20} = -10.9°$ (c=15 mg/ml), 32. (+)-1(3,3-diphenylpropyl)-3-[2-hydroxy-3(4-fluorophenoxy)propyl]piperazine, di-hydrochloride $C_{28}H_{33}FN_2O_2 \cdot 2HCl$, melting point 230°–233° C., $[\alpha]_{589\ mm}^{20} = +10.6°$ (methanol=15 mg/ml), 33. 1-[4,4-bis(4-fluorophenyl)butyl]-4-(2-hydroxy-3(4-fluorophenoxy)propyl]homopiperazine 5.9 g (0.022 mol) of 1-[2-hydroxy-3-(4-fluorophenoxy)propyl]homopiperazine and 6.2 g (0.022 mol) of 4,4-bis(4-fluorophenyl)butyl chloride were dissolved with 3.2 g of calcium carbonate in 100 ml of toluene and heated to boiling under reflux with stirring for 2.5 h. After cooling, filtration with suction was carried out, the solvent was removed by distillation under reduced pressure, and the residue was purified by column chromatography. (Silica gel, eluent methylene chloride with 4% methanol). Yield 4.0 g, oxalate, $C_{30}H_{35}F_3N_2O_2 \cdot 2 C_2H_2O_4$, melting point 160°–165° C.

34. Reaction in analogy to Example 1 of 1-[4,4-bis(4-fluorophenyl)butyl]piperazine with 3-(4-fluorothiophenoxy)1,2-epoxypropane (obtained by reaction of 4-fluoro-thiophenol with epichlorohydrin)-resulted in 1-[4,4-bis(4-fluorophenyl)butyl]-4-[2-hydroxy-3-(4-fluoro-thiophenoxy)propyl]piperazine, di-hydrochloride $C_{29}H_{33}F_3N_2OS \cdot 2HCl$, melting point 212°–215° C.

The following was prepared in the same way:

35. 1-(3,3-diphenylpropyl)-3-[(2-hydroxy-3-thiophenoxy)propyl]piperazine, di-hydrochloride $C_{28}H_{34}N_2OS \cdot 2HCl$, melting point 236°–240° C.

The effect of the novel substances was measured as follows:

1. Protection from acute cerebral hypoxia

Female mice (weight 22–28 g) were placed in a glass tube (diameter 6 cm) through which was passed a mixture of 3.5 parts of oxygen and 96.5 parts of nitrogen. Untreated control animals survived 138 sec. on average in a glass tube of this type. The dose of active substances which, after intraperitoneal administration thereof, increases the survival time of the animals by 50% was determined.

2. Protection from global cerebral ischemia

Female mice (weight 24–27 g) received the active substance intraperitoneally before administration of 0.1 ml of an 80% strength solution (g/l) of $MgCl_2 \cdot 6H_2O$. Untreated control animals survive 24 sec. on average after administration of MgCl₂. The dose of active substances which increases the survival time of the animals by 50% compared with placebo-treated animals was determined.

3. Affinity of the test substances to the calcium channel.

The affinity of the test substances to the calcium channel was determined by inhibition of the specific (S)-³H-devapamil binding to guinea-pig skeletal muscle membranes (FEBS Lett. 176, 371 (1984)). For this, the membranes were incubated with a fixed concentration of 1 nM (S)-³H-devapamil and increasing concentrations of test substance in 50 mM tris-HCl/0.1 mM phenylmethylsulfonyl fluoride, (pH 7.4) at 20° C. for 60 minutes. The non-specific binding was determined using 10⁻⁶M (S)-devapamil. The mixtures were then filtered through glass fiber filters, and the amount of (S)-³H-devapamil retained on the filter was determined by liquid scintillation measurement. The Ki values were determined by non-linear regression analysis.

The table which follows shows the results obtained in the abovementioned tests. The comparison substances used were the substances flunarizine and lidoflazine, which are active ingredients of commercial products.

TABLE

| Substance of Example No. | Test 1 mg/kg i.p. ED 50% | Test 2 mg/kg i.p. ED 50% | Test 3 Ki (nM) |
| --- | --- | --- | --- |
| 1 | 11 | 27 | 8 |
| 2 | 11 | 20 | 9.1 |
| 3 | 10 | 13 | 8 |
| 4 | 6.6 | 8.6 | 18 |
| 7 | 4.6 | 10 | 280 |
| 8 | 5.0 | 13 | 160 |
| 9 | 7.3 | 12 | 30 |
| 11 | 4.9 | 46 | 8 |
| 12 | 4.7 | 45 | 16 |
| 13 | 6.9 | 39 | 10 |
| 16 | 5.5 | 38 | 11 |
| 17 | 16 | 27 | 10 |
| 22 | 6.0 | 8.8 | 15 |
| 23 | 8.6 | 41 | 22 |
| 24 | 23 | 40 | 12 |
| 27 | 14 | 29 | 22 |
| 29 | 1.6 | 13 | 9 |
| 30 | 4.0 | 17 | 10 |
| 31 | 4.1 | 9.3 | 149 |
| 32 | 4.2 | 9.5 | 249 |
| 33 | 4.8 | 31 | 13 |
| 34 | 9.0 | 28 | 9 |

TABLE-continued

| Substance of Example No. | Test 1 mg/kg i.p. ED 50% | Test 2 mg/kg i.p. ED 50% | Test 3 Ki (nM) |
| --- | --- | --- | --- |
| 35 | 8.7 | 14 | 159 |
| flunarizine | >100 | 26.5 | 288 |
| lidoflazine | 10 | >46 | 20 |

We claim:
1. A piperazine of the formula I

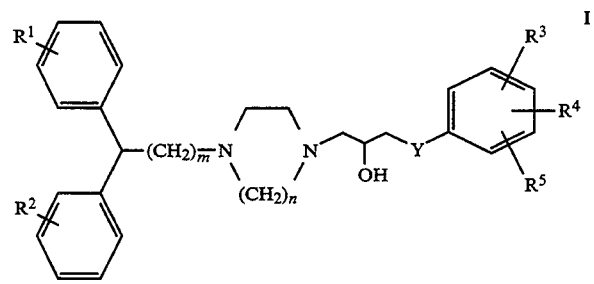

in which
$R^1$ and $R^2$ denote hydrogen, fluorine or chlorine atoms,
$R^3$, $R^4$ and $R^5$ denote hydrogen, fluorine or chlorine atoms,
Y denotes an oxygen or sulfur atom,
m denotes 3 and
n denotes 2,
or the salts thereof with physiologically tolerated acids.

2. The piperazine of claim 1 which is 1-[4,4-bis(4-Fluorophenyl)butyl]-4-[2-hydroxy-3-(4-fluorophenoxy)propyl]piperazine.

3. The piperazine of claim 1 which is (−)-1-[4,4-bis(4-Fluorophenyl)butyl]-4-[2-hydroxy-3-[4-fluorophenoxy)propyl]piperazine.

4. The piperazine of claim 1 which is (+)-1-[4,4-bis(4-Fluorophenyl)butyl]-4-[2-hydroxy-3-(4-fluorophenoxy)propyl]piperazine.

5. A pharmaceutical composition for the treatment of oxygen deficiency states of the brain which comprises an effective amount of a piperazine of the formula I of claim 1.

6. A method for treating patients with oxygen deficiency states of the brain, which comprises administering to the patients an effective amount of a compound of the formula I as claimed in claim 1.

* * * * *